US009119792B2

(12) United States Patent
Bhatt et al.

(10) Patent No.: US 9,119,792 B2
(45) Date of Patent: *Sep. 1, 2015

(54) MODIFIED RELEASE PREPARATIONS CONTAINING OXCARBAZEPINE AND DERIVATIVES THEREOF

(71) Applicant: Supernus Pharmaceuticals, Inc., Rockville, MD (US)

(72) Inventors: Padmanabh P. Bhatt, Rockville, MD (US); Argaw Kidane, Montgomery Village, MD (US); Kevin Edwards, Lovettsville, VA (US)

(73) Assignee: Supernus Pharmaceuticals, Inc., Rockville, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/445,234

(22) Filed: Jul. 29, 2014

(65) Prior Publication Data

US 2015/0094301 A1      Apr. 2, 2015

Related U.S. Application Data

(60) Continuation of application No. 14/103,103, filed on Dec. 11, 2013, now Pat. No. 8,821,930, which is a continuation of application No. 13/476,337, filed on May 21, 2012, now Pat. No. 8,617,600, which is a continuation of application No. 13/137,382, filed on Aug. 10, 2011, now Pat. No. 8,211,464, which is a division of application No. 12/230,275, filed on Aug. 27, 2008, now Pat. No. 8,017,149, which is a continuation of application No. 11/734,874, filed on Apr. 13, 2007, now Pat. No. 7,722,898.

(60) Provisional application No. 60/794,837, filed on Apr. 26, 2006.

(51) Int. Cl.
| | |
|---|---|
| *A61K 9/14* | (2006.01) |
| *A61K 9/20* | (2006.01) |
| *A61K 9/00* | (2006.01) |
| *A61K 31/55* | (2006.01) |

(52) U.S. Cl.
CPC ............. *A61K 9/2054* (2013.01); *A61K 9/0073* (2013.01); *A61K 9/205* (2013.01); *A61K 9/2013* (2013.01); *A61K 9/2027* (2013.01); *A61K 9/2031* (2013.01); *A61K 31/55* (2013.01); *A61K 2800/56* (2013.01)

(58) Field of Classification Search
CPC ................................................. A61K 2800/56
See application file for complete search history.

(56) References Cited

U.S. PATENT DOCUMENTS

| | | | |
|---|---|---|---|
| 3,642,775 | A | 2/1972 | Schindler |
| 3,716,640 | A | 2/1973 | Schindler |
| 4,792,452 | A | 12/1988 | Howard et al. |
| 4,968,508 | A | 11/1990 | Oren et al. |
| 5,147,655 | A | 9/1992 | Ibsen |
| 5,326,570 | A | 7/1994 | Rudnic et al. |
| 5,472,714 | A | 12/1995 | Bourquin |
| 5,700,832 | A | 12/1997 | Baik et al. |
| 5,906,832 | A | 5/1999 | Jao et al. |
| 5,912,013 | A | 6/1999 | Rudnic et al. |
| 5,980,942 | A | 11/1999 | Katzhendler et al. |
| 6,287,599 | B1 | 9/2001 | Burnside et al. |
| 6,296,873 | B1 | 10/2001 | Katzhendler et al. |
| 6,572,889 | B1 | 6/2003 | Guo |
| 7,183,272 | B2 | 2/2007 | Aronhime et al. |
| 7,858,122 | B2 | 12/2010 | Kshirsagar et al. |
| 2001/0001658 | A1 | 5/2001 | Chen et al. |
| 2002/0022056 | A1 | 2/2002 | Schlutermann |
| 2002/0155067 | A1 | 10/2002 | MacGregor |
| 2002/0169145 | A1 | 11/2002 | Shah et al. |
| 2003/0175341 | A1 | 9/2003 | Rampal et al. |
| 2003/0180352 | A1 | 9/2003 | Patel et al. |
| 2003/0180362 | A1 | 9/2003 | Park et al. |
| 2003/0190361 | A1 | 10/2003 | Schlutermann |
| 2004/0142033 | A1 | 7/2004 | Franke et al. |
| 2004/0185095 | A1 | 9/2004 | Franke et al. |
| 2004/0197402 | A1 | 10/2004 | Sehgal et al. |
| 2005/0148594 | A1 | 7/2005 | Cink et al. |
| 2005/0202088 | A1 | 9/2005 | Hanshermann et al. |
| 2005/0255156 | A1 | 11/2005 | MacGregor |
| 2005/0271716 | A1 | 12/2005 | Murai |

(Continued)

FOREIGN PATENT DOCUMENTS

| | | |
|---|---|---|
| CN | 1625390 A | 6/2005 |
| EP | 0 282 571 B1 | 8/1993 |

(Continued)

OTHER PUBLICATIONS

Ahmed et al., "Preparation and evaluation of sustained release carbamazepine matrix tablets using Eudragit RS 100 and Tragacanth," Bull. Pharm. Sci., Assiut University, 2001, 24(1):73-82.

(Continued)

*Primary Examiner* — Paul Dickinson
(74) *Attorney, Agent, or Firm* — Foley & Lardner LLP; Sunit Talapatra

(57) ABSTRACT

Controlled-release preparations of oxcarbazepine and derivatives thereof for once-a-day administration are disclosed. The inventive compositions comprise solubility- and/or release enhancing agents to provide tailored drug release profiles, preferably sigmoidal release profiles. Methods of treatment comprising the inventive compositions are also disclosed.

20 Claims, 14 Drawing Sheets

(56) References Cited

U.S. PATENT DOCUMENTS

| | | | |
|---|---|---|---|
| 2006/0057203 | A1 | 3/2006 | Wolf et al. |
| 2006/0111343 | A1 | 5/2006 | Krishnan et al. |
| 2006/0134196 | A1 | 6/2006 | Rosenberg et al. |
| 2007/0059354 | A1 | 3/2007 | Ramakrishnan et al. |
| 2007/0092559 | A1 | 4/2007 | Yuan et al. |
| 2007/0104778 | A1 | 5/2007 | Zeng et al. |
| 2007/0254033 | A1 | 11/2007 | Bhatt et al. |
| 2009/0004263 | A1 | 1/2009 | Bhatt et al. |
| 2009/0005360 | A1 | 1/2009 | Bhatt et al. |

FOREIGN PATENT DOCUMENTS

| | | |
|---|---|---|
| EP | 0 646 374 A1 | 4/1995 |
| JP | H06-199657 A | 7/1994 |
| WO | WO 97/18814 A1 | 5/1997 |
| WO | WO 02/09675 A1 | 2/2002 |
| WO | WO 02/094774 A2 | 11/2002 |
| WO | WO 03/084513 A1 | 10/2003 |
| WO | WO 03/101430 A1 | 12/2003 |
| WO | WO 2004/026314 A1 | 4/2004 |

OTHER PUBLICATIONS

Collins et al., "Extended Release Formulations of Anticonvulsant Medications," CNS Drugs, Sep. 2000, 14(3):203-212.

DeGussa, Pharma Polymers News, 2003, 10:1-4.

Flesch et al., "Oxcarbazepine final market image tablet formulation bioequivalence study after single administration and at steady state in healthy subjects," International Journal of Clinical Pharmacology and Therapeutics, 2002, 40(11)4:524-532.

http://www.merriam-wester.com/dictionary/matrix (accessed Dec. 8, 2008), 3 pages.

Kibbe, Arthur H., Ph.D., Ed., "Polymethacrylates," Handbook of Pharmaceutical Excepients, Third Edition, 2000, 401-406.

Merriam-Webster online dictionary, Dec. 8, 2008, "matrix", http://www.merriamwebster.com/dictionary/matrix, Dec. 8, 2008, 3 pages.

Nokhodchi et al., "The effect of various surfactants on the release rate of propranolol hydrochloride from hydroxypropylmethylcellulose (HPMC)-Eudagrit matrices," European Journal of Pharmaceutics and Biopharmaceutics, 2002, 54:349-356.

Notice of Allowance of prior application U.S. Appl. No. 11/734,874, Feb. 23, 2010.

Notice of Allowance of prior application U.S. Appl. No. 14/103,103, May 1, 2014.

Rowe, Raymond C., Ed., "Polymethacrylates," Handbook of Pharmaceutical Excipients, Fourth Edition, 2003, 462-468.

Sheskey et al., "Roll Compaction Granulation of a Controlled-Release Matrix Tablet Formaulation Containing HPMC, Effect of Process Scale-Up on Robustness of Tablets, Tablet Stability, and Predicted In Vivo Performance," Pharmaceutical Technology, Nov. 2000, 30-50.

Walker et al., "Clinical Pharmacokinetics of New Antiepileptic Drugs," Pharmac. Ther., 1995, 67(3):351-384.

Wellington et al., "Oxcarbazepine: An Update of Its Efficacy in the Management of Epilepsy," CNS Drugs, 2001, 15(2):137-163.

MODIFIED RELEASE PREPARATIONS CONTAINING OXCARBAZEPINE AND DERIVATIVES THEREOF

CROSS REFERENCE TO RELATED APPLICATIONS

This application is a Continuation of U.S. application Ser. No. 14/103,103, filed Dec. 11, 2013, which is a Continuation of U.S. application Ser. No. 13/476,337, filed May 21, 2012, which is a Continuation of U.S. application Ser. No. 13/137,382, filed Aug. 10, 2011, now U.S. Pat. No. 8,211,464, which is a Continuation of U.S. application Ser. No. 12/230,275, filed Aug. 27, 2008, now U.S. Pat. No. 8,017,149, which is a Continuation of U.S. application Ser. No. 11/734,874, filed Apr. 13, 2007, now U.S. Pat. No. 7,722,898, issued May 25, 2010, which claims priority to U.S. Provisional Application No. 60/794,837, filed Apr. 26, 2006, the disclosures of which are incorporated herein by reference in their entirety.

FIELD OF THE INVENTION

The present invention is directed to controlled-release preparations of oxcarbazepine and derivatives thereof for once-a-day administration.

BACKGROUND OF THE INVENTION

Oxcarbazepine belongs to the benzodiazepine class of drugs and is registered worldwide as an antiepileptic drug. Oxcarbazepine is approved as an adjunct or monotherapy for the treatment of partial seizures and generalized tonic-clonic seizures in adults and children. An immediate-release (IR) formulation of oxcarbazepine is currently on the market under the trade name Trileptal® and is administered twice a day to control epileptic seizures. Such immediate release compositions provide the drug to the patient in a manner that result in a rapid rise of the plasma drug concentration followed by a rapid decline. This sharp rise in drug concentration can result in side effects, and make multiple daily administration of the drug necessary in order to maintain a therapeutic level of the drug in the body. The need for a controlled-release dosage form for drugs taken chronically such as oxcarbazepine and derivatives is self-evident. Patient compliance is greatly improved with controlled-release (CR) dosage forms that are taken, for example, once-a-day. Also, there are significant clinical advantages such as better therapeutic efficacy as well as reduced side effects with controlled-release dosage forms.

Oxcarbazepine and its derivatives contemplated in this invention are poorly soluble in water. Due to their poor solubility, their release from a sustained release dosage form is rather incomplete. Whereas the in vitro release of oxcarbazepine is dependent on the dissolution method, including the dissolution media used, it has been found through in silico modeling that the release of oxcarbazepine in vivo from a traditional sustained-release dosage form is relatively low. This results in reduced bioavailability of the drug making the dosage form ineffective in providing a therapeutically effective concentration in the body. This poses a serious challenge to the successful development of sustained-release dosage forms for oxcarbazepine and its derivatives.

The rate of drug release from a dosage form has a significant impact on the therapeutic usefulness of the drug and its side effects. Hence, drug release profiles must be customized to meet the therapeutic needs of the patient. An example of a customized release profile is one that exhibits a sigmoidal release pattern, characterized by an initial slow release followed by fast release which is then followed by slow release until all of the drug has been released from the dosage form.

Sustained-release dosage forms for oxcarbazepine and derivatives have been described in the art. For example, Katzhendler et al. (U.S. Pat. No. 6,296,873) describes sustained-release delivery systems for carbamazepine and its derivatives. Katzhendler et al. teaches that a zero-order release profile is achieved for carbamazepine and derivatives through the use of hydrophilic and hydrophobic polymers. Zero-order (constant) release was achieved using high molecular weight hydroxypropyl methyl cellulose (HPMC) along with some optional hydrophobic excipients. A similar approach is taught by Shah et al. (US Patent Application 20020169145). Franke et al. (US Patent Application 20040142033) discloses sustained-release formulations of oxcarbazepine that are characterized by the release of 55%-85% of the drug in 15 minutes, and up to 95% in 30 minutes. According to the authors, such release profiles provide adequate sustained-release to achieve once-a-day administration of oxcarbazepine. However, the solubility and bioavailability of the drug from these enhanced preparations suitable for once-a-day administration. The prior art does not teach how to make preparations of oxcarbazepine and derivatives characterized by sigmoidal release profiles.

SUMMARY OF THE INVENTION

It is an object of this invention to provide controlled-release formulations of oxcarbazepine for once-a-day administration. The composition of this invention is administered once-a-day and yet meets the therapeutic need of the patient. It is another object of this invention to improve the bioavailability of oxcarbazepine and derivatives thereof. It is yet another object of this invention to meet the therapeutic need of the patient without causing "spikes" in blood drug concentration that may lead to toxicity. It is yet another object of this invention to keep the blood concentration of the drug within the therapeutic window. It is yet another object of this invention to minimize the fluctuation between the $C_{max}$ and $C_{min}$ that is typical of many immediate-release and sustained-release preparations.

Many, if not all, of these objectives may be achieved in this invention through formulations that comprise both solubility-enhancing agents and release-promoting agents, and are characterized by release profiles that meet the requirement for once-a-day administration. The objectives may also be achieved through the combination of a multiplicity of units with different release profiles in one dosage unit. Minipellets/granules/tablets, which can be mixed in a certain ratio, provide a dosage form that meets the above stated therapeutic objectives.

This invention also pertains to multi-layer tablets. Multi-layer tablets can be prepared with each layer releasing the drug at a rate that is different from the rate of release from another layer. In multi-layer tablets, each layer may or may not be coated.

All of the advantages that stem from once-daily administration of a drug apply to the compositions of this invention. Some of the specific advantages of this invention may be: reduced fluctuation between $C_{max}$ and $C_{min}$ during the course of treatment and hence better therapeutic profile, reduced side-effects, improved patient compliance, and improved bioavailability of the drug.

DETAILED DESCRIPTION OF THE INVENTION

Figure 1:
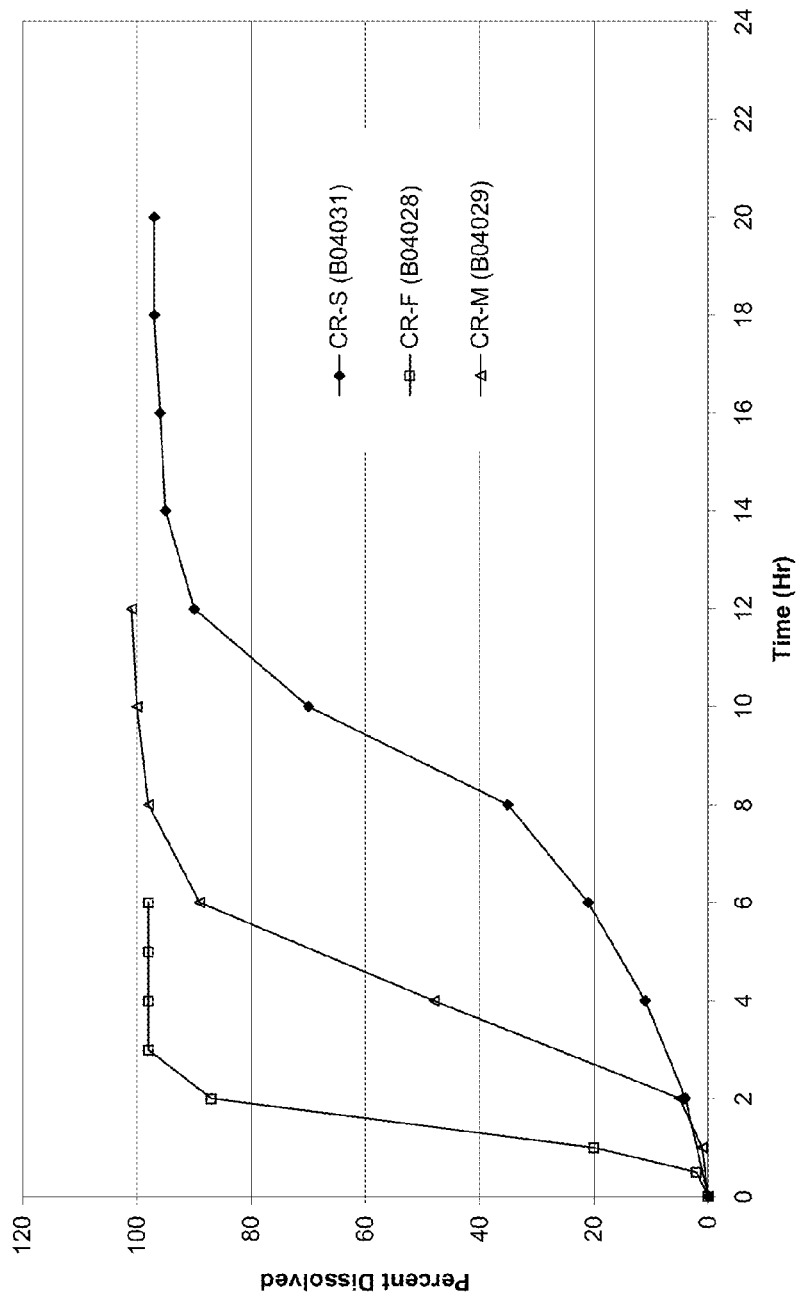
FIG. 1 shows the dissolution profiles for the three exemplary (CR-F, CR-M, and CR-S) oxcarbazepine formulations containing no solubility/release enhancer. The profiles show a non-zero order release with a lag. The $T_{80}$s (time for 80% of the dose to be released in vitro) for the CR-F, CR-M, and CR-S formulations were 2 Hrs, 5 Hrs and 11 Hrs, respectively. USP Apparatus II at 60 RPM was used. Dissolution medium was 1% SLS in water.

It is the object of this invention to provide controlled-release oxcarbazepine formulations suitable for once-a-day administration. It is an additional object of the invention to incorporate a combination of solubility-enhancing excipients and/or release-promoting agents into the formulations to enhance the bioavailability of oxcarbazepine and its derivatives. Such compositions are referred to as enhanced formulations.

Oxcarbazepine was formulated to provide release profiles characterized by slow release initially, followed by rapid release and then followed by another period of slow release. Such a release profile is known to those skilled in the art as sigmoidal. Oxcarbazepine formulations with sigmoidal release profiles were tested in human pharmacokinetic (PK) studies. Based on the human data, improvements were made to the formulations by incorporating solubility enhancers and/or release-promoting excipients (such formulation are referred to as enhanced formulations). The enhanced formulations were tested in canine models and were surprisingly found to provide significant increase in bioavailability of oxcarbazepine compared to formulations containing no solubility/release enhancing excipients.

The incorporation of solubility enhancing agents in formulations containing poorly soluble drugs such as oxcarbazepine has a profound effect on the in vivo solubility and hence bioavailability of the drugs. Enhancing the solubility of oxcarbazepine results in an increase in its bioavailability and hence in better therapeutic performance of the drug. A combination of solubility and release promoters is contemplated in this invention. Preferable release promoting agents are pH dependent polymers, also known as enteric polymers. These materials are well known to those skilled in the art and exhibit pH dependent solubility such that they dissolve at pH values higher than about 4.0, while remaining insoluble at pH values lower than 4.0. Solubilizers function by increasing the aqueous solubility of a poorly soluble drug. When a formulation containing both the enteric polymer and solubilizer is exposed to an aqueous media of pH higher than 4.0, the enteric polymer dissolves rapidly leaving a porous structure, resulting in increased contact surface between the aqueous medium and the poorly soluble drug. This increased surface area enhances the efficiency of the solubilizer(s), and hence, the overall solubility and release rate of the drug is enhanced to a point where it impacts the availability of the drug for systemic absorption in patients.

Excipients that function as solubility enhancers can be ionic and non-ionic surfactants, complexing agents, hydrophilic polymers, pH modifiers, such as acidifying agents and alkalinizing agents, as well as molecules that increase the solubility of poorly soluble drug through molecular entrapment. Several solubility enhancers can be utilized simultaneously. All enteric polymers that remain intact at pH value lower than about 4.0 and dissolve at pH values higher than 4.0, preferably higher than 5.0, most preferably about 6.0, are considered useful as release-promoting agents for this invention.

Suitable pH-sensitive enteric polymers include cellulose acetate phthalate, cellulose acetate succinate, methylcellulose phthalate, ethylhydroxycellulose phthalate, polyvinylacetate phthalate, polyvinylbutyrate acetate, vinyl acetate-maleic anhydride copolymer, styrene-maleic monoester copolymer, methyl acrylate-methacrylic acid copolymer, methacrylate-methacrylic acid-octyl acrylate copolymer, etc. These may be used either alone or in combination, or together with the polymers other than those mentioned above. Preferred enteric polymers are the pharmaceutically acceptable methacrylic acid copolymers. These copolymers are anionic polymers based on methacrylic acid and methyl methacrylate and, preferably, have a mean molecular weight of about 135000. A ratio of free carboxyl groups to methyl-esterified carboxyl groups in these copolymers may range, for example, from 1:1 to 1:3, e.g. around 1:1 or 1:2. Such polymers are sold under the trade name Eudragit™ such as the Eudragit L series e.g. Eudragit L 12.5™, Eudragit L 12.5P™, Eudragit L100™, Eudragit L 100-55™, Eudragit L-30D™, Eudragit L-30 D-55™, the Eudragit S™ series e.g. Eudragit S 12.5™, Eudragit S 12.5P™, Eudragit S100™. The release promoters are not limited to pH dependent polymers. Other hydrophilic molecules that dissolve rapidly and leach out of the dosage form quickly leaving a porous structure can be also be used for the same purpose.

The release-promoting agent can be incorporated in an amount from 10% to 90%, preferably from 20% to 80% and most preferably from 30% to 70% by weight of the dosage unit. The agent can be incorporated into the formulation either prior to or after granulation. The release-promoting agent can be added into the formulation either as a dry material, or it can be dispersed or dissolved in an appropriate solvent, and dispersed during granulation.

Solubilizers preferred in this invention include surface active agents such as sodium docusate, sodium lauryl sulfate, sodium stearyl fumarate, Tweens® and Spans (PEO modified sorbitan monoesters and fatty acid sorbitan esters), poly(ethylene oxide)-polypropylene oxide-poly(ethylene oxide) block copolymers (aka Pluronics™); complexing agents such as low molecular weight polyvinyl pyrrolidone and low molecular weight hydroxypropyl methyl cellulose; molecules that aid solubility by molecular entrapment such as cyclodextrins, and pH modifying agents, including acidifying agents such as citric acid, fumaric acid, tartaric acid, and hydrochloric acid; and alkalizing agents such as meglumine and sodium hydroxide.

Solubilizing agents typically constitute from 1% to 80% by weight, preferably from 1% to 60%, more preferably from 1% to 50%, of the dosage form and can be incorporated in a variety of ways. They can be incorporated in the formulation prior to granulation in dry or wet form. They can also be added to the formulation after the rest of the materials are granulated or otherwise processed. During granulation, solubilizers can be sprayed as solutions with or without a binder.

This invention also contemplates controlled-release formulations comprising oxcarbazepine that release the drug at variable rates in the GI tract. It is also an object of this invention to design a drug delivery system to deliver drug at a very low rate early, followed by a relatively increased rate. It is another object of this invention to provide a drug release profile that is characterized by an immediate-release followed by a modified-release, such as extended-release (XR) or delayed-release (DR). These types of release profiles ensure that the $C_{max}$ (maximum concentration of the drug in blood/plasma) is kept within the therapeutic window while extending the maintenance of an effective drug level in the body. The goal of this invention is to develop a controlled-release pharmaceutical composition of oxcarbazepine that provides steady-state blood levels of MHD, an active metabolite of oxcarbazepine, at a concentration of about 2 µg/ml to about 10 µg/ml. In the preferred embodiment, steady-state blood $C_{max}$ levels of MHD fall in the range of about 6 µg/ml to about 10 µg/ml, and $C_{min}$ levels of MHD fall in the range of about 2 µg/ml to about 5 µg/ml. Reduced fluctuation between $C_{max}$ and $C_{min}$ during the course of treatment results in a better therapeutic profile, reduced side-effects, improved patient compliance, and improved bioavailability of the drug.

The desired drug release pattern contemplated by this invention is achieved by using "matrix" polymers that hydrate and swell in aqueous media, such as biological fluids. As these polymers swell, they form a homogenous matrix structure that maintains its shape during drug release and serves as a carrier for the drug, solubility enhancers and/or release promoters. The initial matrix polymer hydration phase results in slow-release of the drug (lag phase). Once the polymer is fully hydrated and swollen, the porosity of the matrix increases due to the leaching out of the pH-dependent release promoters, and drug is released at a faster rate. The rate of the drug release then becomes constant, and is a function of drug diffusion through the hydrated polymer gel.

Thus, the release vs. time curve is characterized by at least two slopes: one slope for the lag phase where drug release rate is low and a second slope where drug release is faster. The slope of the rising part of the release vs. time curve can be customized as to match the rate at which the drug is eliminated from the body. A desired release profile can be achieved by using swellable polymers alone or in combination with binders, such as gelling and/or network forming polymers.

The water-swellable, matrix forming polymers useful in the present invention are selected from a group comprising cellulosic polymers, such as hydroxypropylmethylcellulose (HPMC), hydroxypropylcellulose (HPC), hydroxyethylcellulose (HEC), methylcellulose (MC), powdered cellulose such as microcrystalline cellulose, cellulose acetate, sodium carboxymethylcellulose, calcium salt of carboxymethylcellulose, and ethylcellulose; alginates, gums such as guar and xanthan gums; cross-linked polyacrylic acid derivatives such as Carbomers (aka Carbopol™) available in various molecular weight grades from Noveon Inc. (Cincinnati, Ohio); carageenan; polyvinyl pyrrolidone and its derivatives such as crospovidone; polyethylene oxides; and polyvinyl alcohol. Preferred swellable polymers are the cellulosic compounds, HPMC being the most preferred.

The swellable polymer can be incorporated in the formulation in proportion from 1% to 50% by weight, preferably from 5% to 40% by weight, most preferably from 5% to 20% by weight. The swellable polymers and binders may be incorporated in the formulation either prior to or after granulation. The polymers can also be dispersed in organic solvents or hydro-alcohols and sprayed during granulation.

It is yet another aspect of this invention to prepare formulations of oxcarbazepine that combine multiple modified-release "units," each "unit" prepared according to any one or more of the above-disclosed dosage forms, to provide for a customized release profile.

The modified-release units comprise minipellets/granules/tablets etc., each with unique release profiles, that can be mixed in a certain ratio to provide a dosage form that meets the above-stated therapeutic objectives. Alternatively, multiple modified release units may be formed into of multi-layer tablets. Multi-layer tablets can be prepared with each layer releasing the active compound at a rate that is different from the rate of release of the active ingredient from another layer. In multi-layer tablets, each layer may optionally be coated with controlled-release polymer(s). The combination dosage forms can exhibit release profiles that comprise any/all possible combinations of immediate release (IR), delayed release (DR), and extended release (XR) formulations. Pellets/granules/tablets or each layer of a single tablet may optionally be coated.

Various hydrophobic excipients can be used to modify the hydration rate of the dosage unit when exposed to water or aqueous media. These excipients retard the wetting of the dosage unit and hence modify the release of the active agent. Hydrophobic excipients suitable for this invention are represented by, but not limited to, glyceryl monstearate, mixtures of glyceryl monostearate and glyceryl monopalmitate (Myvaplex, Eastman Fine Chemical Company), glycerylmonooleate, a mixture of mono, di and tri-glycerides (ATMUL 84S), glycerylmonolaurate, glyceryl behenate, paraffin, white wax, long chain carboxylic acids, long chain carboxylic acid esters and long chain carboxylic acid alcohols.

Examples of saturated straight chain acids, useful with the invention, are n-dodecanoic acid, n-tetradecanoic acid, n-hexadecanoic acid, caproic acid, caprylic acid, capric acid, lauric acid, myristic acid, palmitic acid, stearic acid, arachidic acid, behenic acid, montanic acid and melissic acid. Also useful are unsaturated monoolefinic straight chain monocarboxylic acids. Examples of these are oleic acid, gadoleic acid and erucic acid. Also useful are unsaturated (polyolefinic) straight chain monocarboxylic acids such as linoleic acid, linolenic acid, arachidonic acid and behenolic acid. Useful branched acids include, for example, diacetyl tartaric acid.

Examples of long chain carboxylic acid esters include, but are not limited to: glyceryl monostearates; glyceryl monopalmitates; mixtures of glyceryl monostearate and glyceryl monopalmitate (Myvaplex 600, Eastman Fine Chemical Company); glyceryl monolinoleate; glyceryl monooleate; mixtures of glyceryl monopalmitate, glyceryl monostearate, glyceryl monooleate and glyceryl monolinoleate (Myverol 18-92, Eastman Fine Chemical Company); glyceryl monolinoleate; glyceryl monoadoleate; mixtures of glyceryl monopalmitate, glyceryl monostearate, glyceryl monooleate, glyceryl monolinoleate, glyceryl monolinoleate and glyceryl monogadoleate (Myverol 18-99, Eastman Fine Chemical Company); acetylated glycerides such as distilled acetylated monoglycerides (Myvacet 5-07, 7-07 and 9-45, Eastman Fine Chemical Company); mixtures of propylene glycol monoesters, distilled monoglycerides, sodium stearoyl lactylate and silicon dioxide (Myvatex TL, Eastman Fine Chemical Company); mixtures of propylene glycol monoesters, distilled monoglycerides, sodium stearoyl lactylate and silicon dioxide (Myvatex TL, Eastman Fine Chemical Company), d-alpha tocopherol polyethylene glycol 1000 succinate (Vitamin E TPGS, Eastman Chemical Company); mixtures of mono- and diglyceride esters such as Atmul (Humko Chemical Division of Witco Chemical); calcium stearoyl lactylate; ethoxylated mono- and di-glycerides; lactated mono- and di-glycerides; lactylate carboxylic acid ester of glycerol and propylene glycol; lactylic esters of long chain carboxylic acids; polyglycerol esters of long chain carboxylic acids, propylene glycol mono- and di-esters of long chain carboxylic acids; sodium stearoyl lactylate; sorbitan monostearate; sorbitan monooleate; other sorbitan esters of long chain carboxylic acids; succinylated monoglycerides; stearyl monoglyceryl citrate; stearyl heptanoate; cetyl esters of waxes; cetearyl octanoate; $C_{10}$-$C_{30}$ cholesterol/lavosterol esters; and sucrose long chain carboxylic acid esters. In addition, waxes can be useful alone or preferably in combination with the materials listed above. Examples of these are white wax, paraffin and carnauba wax.

Drug, polymers, and other excipients are typically combined and wet granulated using a granulating fluid. However, other methods of forming granules such as slugging, and roller compaction can also be used to manufacture matrix granules. Matrix tablets can also be made by direct compression. In wet granulation, typical granulating fluids are: water, a mixture of water and alcohol, anhydrous alcohol. Wet granules can be made in any granulating device such as mixers, high shear granulators, and fluid bed granulators. Granules can be dried in appropriate drying equipment such as fluid bed dryers, ovens, microwave dryers etc. Granules can also be air-dried. Dried granules can be milled using appropriate milling device to achieve a particular particle size distribution. Granules can be filled in to capsules, or blended with other excipients and tableted on a tablet press. Granules can also be packaged into sachets for sprinkle application. Other excipients used to aid tableting are well known to those skilled in the art and include magnesium stearate, talc, cabosil etc. Granules and tablets can, optionally, be coated to further modify release rates. Furthermore, formulations can also optionally contain dyes.

Optionally, but preferably, the tablet composition can contain one or more lubricants, which may be added to assure proper tableting. Non-limiting examples of lubricants include magnesium stearate, calcium stearate, zinc stearate, stearic acid, polyethylene glycol, leucine, glyceryl behenate, sodium stearyl fumarate, hydrogenated vegetable oils, and other waxes, including but not limited to, beeswax, carnuba wax, cetyl alcohol, glyceryl stearate, glyceryl palmitate, and stearyl alcohol. The lubricant, when present, is typically included in an amount of from about 0.1 wt. % to about 20 wt. % of the composition, preferably from about 1 to about 10 wt. %, and more preferably about 0.3 to about 3.0 wt. %.

The oxcarbazepine dosage can be formulated into tablets, granules, and pellets. The steps involved in the manufacturing of these dosage forms are well known to those skilled in the art. Briefly, tablets can be compressed from directly compressible blend containing the active or pre-formed granules. The tablets can be coated or not coated. The coating may optionally impart modification of release. Granules can be made by high shear granulation or fluid bed processing. The granules may or may not be coated. Pellets can be manufactured by drug layering on inert carriers such as sugar spheres. Pellets can also be manufactured by extrusion/spheronization process. The pellets may or may not be coated. Coated pellets and granules can be filled into capsules.

Formulations of this invention can also be made in pelletized forms, which can be filled into capsules or dispensed in sachets for sprinkle application. Each pellet is composed of the drug, swellable polymer(s) and other excipients that aid the processing. Pellets can be prepared in one of the many ways that are known by those skilled in the art. These include, for example, extrusion/spheronization and roller compaction (slugging). In the extrusion/spheronization technique, drug is mixed with swellable polymer(s), such as cellulosic polymers and other excipients. The blend is then granulated in a high shear granulator. The wet mass is then passed through an extruder and spheronized using a spheronizer. The pellets are then dried in an oven or fluid bed processor. The dried pellets are either processed further or encapsulated without further processing.

Unless otherwise defined, all technical and scientific terms used herein have the same meaning as commonly understood by one of ordinary skill in the art to which this invention belongs. All publications, patent applications, patents, and other references mentioned herein are incorporated by reference in their entirety. In case of conflict, the present specification, including definitions, will control. In addition, the materials, methods, and examples are illustrative only and not intended to be limiting.

The invention now will be described in particularity with the following illustrative examples; however, the scope of the present invention is not intended to be, and shall not be, limited to the exemplified embodiments below.

EXAMPLES

Example 1

Oxcarbazepine Formulations with Sigmoidal Release Profiles

Table 1 provides the formula composition of oxcarbazepine controlled-release preparations with sigmoidal release profiles. Granules were prepared by high shear granulation using anhydrous ethanol as the granulating liquid. All ingredients, except for magnesium stearate, were charged in to VG-65/10M high shear granulator. The dry powders are blended by running the blade for 3 minutes, after which time the anhydrous ethanol was sprayed onto the mixing blend at a spray rate of approximately 40-60 gm/min. After about a minute of spray, the chopper on the VG-65/10M was started and run throughout the spray. Once the granulation was completed, the granulation was discharged from the VG high shear granulator, spread on an appropriate tray and placed in an oven to dry at 40° C. for 24 Hrs. Alternatively, granules can be dried using a fluid bed processor. Dry granules were screened through an 18-mesh screen. Screened granules were blended with magnesium stearate in a proportion of 99.5% granules and 0.5% magnesium stearate. The blend was then tableted on a rotary tablet press.

TABLE 1

Formula composition of Oxcarbazepine CR formulations with changing slope

| Ingredients | SLI 530 CR-F (Fast) | SLI530 CR-M (Medium) | SLI530 CR-S (Slow) |
|---|---|---|---|
| Oxcarbazepine | 60 | 60 | 60 |
| Compritol 888ATO | 9.5 | 7 | — |
| Prosolv HD90 | 9.8 | 20.3 | 15 |
| Kollidon 25 | 10 | — | — |
| Kollidon 90 | — | 3 | — |
| Methocel E5 Prem. LV | — | — | 10 |
| Methocel K4M Premium CR | — | — | 5 |
| Carbopol 971P | 10 | 9 | 9 |
| Mg Stearate | 0.5 | 0.5 | 0.5 |
| FD&C Red #40 | — | — | 0.5 |
| FD&C Blue #1 | 0.2 | — | — |
| FD&C Yellow #6 | — | 0.2 | — |
| Anhydrous Ethanol | * | * | * |
| Total | 100 | 100 | 100 |

* Removed during processing

FIG. 1 shows the dissolution profiles of three exemplary oxcarbazepine CR formulations (CR-F, CR-M, and CR-S). The profiles exhibited non-zero order release.

Example 2

Human Pharmacokinetic Evaluation of Oxcarbazepine CR Formulations from Example 1

The three formulations from the Example 1 were evaluated in humans to obtain pharmacokinetic information. An immediate release tablet (Trileptal® 600 mg) was used as a control reference. The formulations were examined in a randomized, single dose, crossover study in healthy human volunteers. Blood samples were analyzed for both the parent molecule oxcarbazepine and its metabolite (the monohydroxy derivative, MHD).

Figure 2:
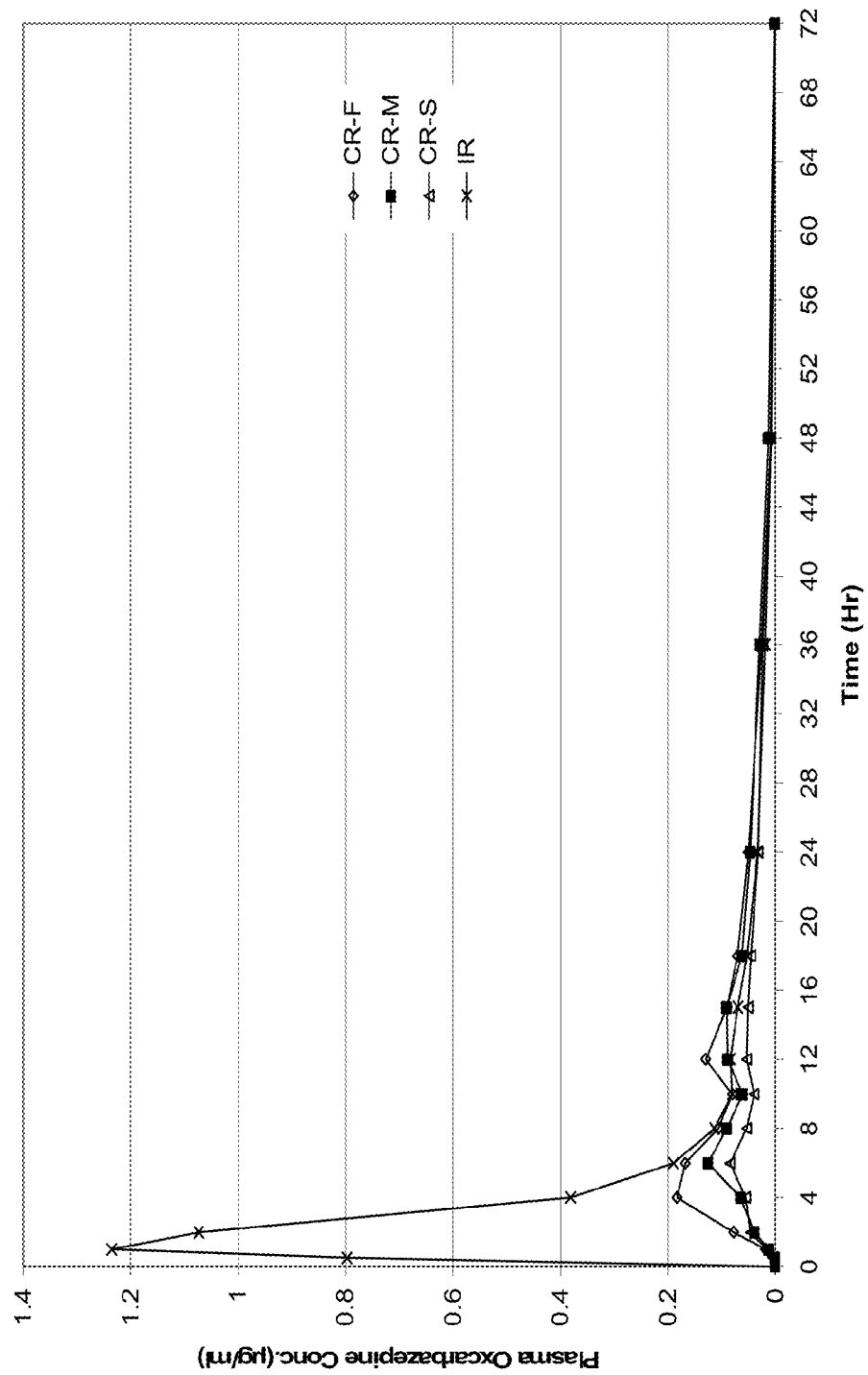
FIG. 2 shows the human pharmacokinetic (PK) profiles with respect to oxcarbazepine for the three exemplary controlled-release formulations of example 1 versus an immediate-release reference product (Trileptal® 600 mg). The strength of each formulation is 600 mg oxcarbazepine per tablet.
Figure 3:
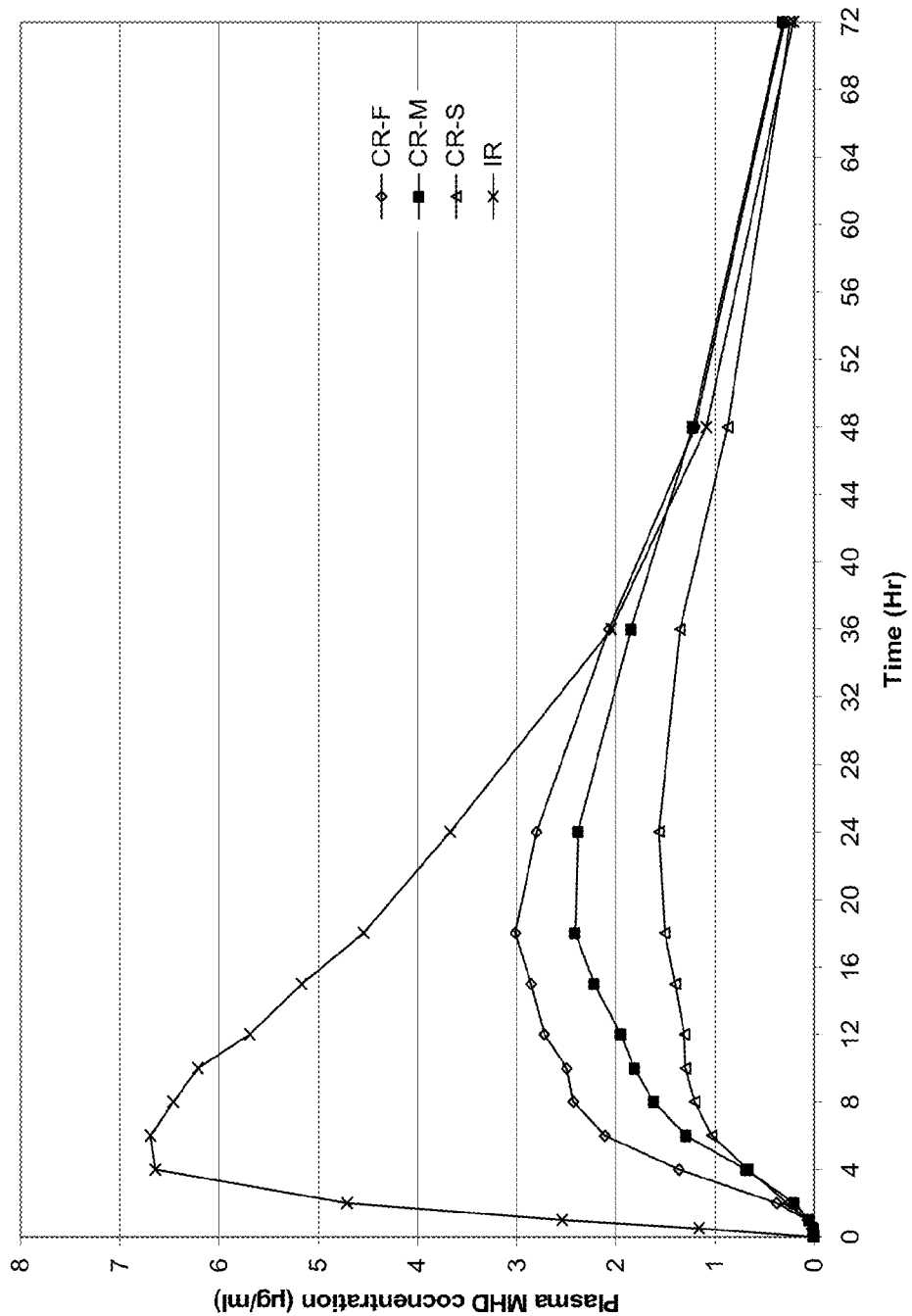
FIG. 3 shows the PK profiles with respect to the metabolite of oxcarbazepine (MHD) for the three exemplary controlled-release formulations of example 1 versus an immediate-release reference product (Trileptal® 600 mg). The strength of each formulation is 600 mg oxcarbazepine per tablet.

Table 2 provides the mean PK parameters for MHD. The PK profiles are shown in FIGS. 2 and 3.

TABLE 2

Pharmacokinetic parameters of the three exemplary formulations in example 1 and immediate release reference product.

| PK Parameters | CR-F Fast | CR-M Med | CR-S Slow | Trileptal ™ IR |
|---|---|---|---|---|
| $T_{max}$ (Hr) | 6.5 | 8.4 | 9.1 | 1.4 |
| $C_{max}$ (ug/mL) | 0.248 | 0.146 | 0.103 | 1.412 |
| $AUC_{last}$ (Hr*ug/mL) | 3.0 | 2.5 | 1.7 | 5.7 |
| Rel BA | 53% | 44% | 30% | 100% |

Example 3

Solubility Enhancers Screening

Figure 4:
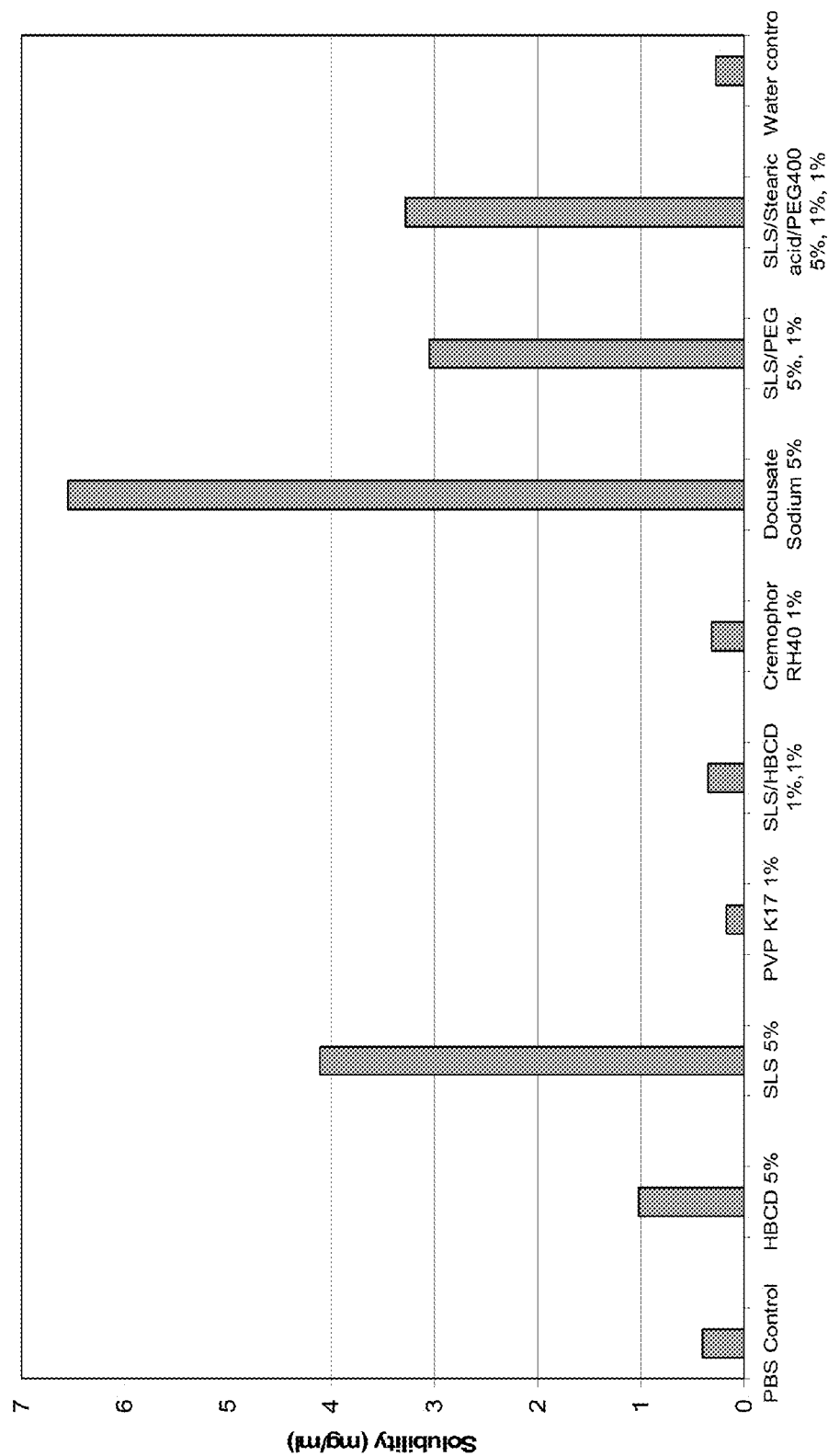
FIG. 4 shows the solubility results of oxcarbazepine with selected excipients.

The solubility of oxcarbazepine in the presence of excipients was evaluated as follows:

Excipients were dissolved in phosphate buffer to make solutions with concentrations shown in Table 3. One gram of oxcarbazepine was then mixed with 19 gm of the excipient solution. The mixture was rocked overnight at room temperature and then filtered using 0.22 μm filter. The filtrates were analyzed by HPLC. The solubility results are given in Table 3 and FIG. 4.

TABLE 3

Solubility of Oxcarbazepine in the presence of excipients

| Excipients | Excipient conc. (% w/w) | Solubility (mg/mL) |
|---|---|---|
| Phosphate Buffer Control | NA | 0.4009 |
| Hydroxypropyl betacyclodextrin (HBCD) | 5 | 1.0218 |
| Sodium Lauryl Sulfate (SLS) | 5 | 4.1113 |
| Kollidon 17 | 1 | 0.1717 |
| SLS/HBCD | 1, 1 | 0.3489 |
| Cremophor RH40 | 1 | 0.3140 |
| Docusate Sodium | 5 | 6.5524 |
| SLS/Polyethylene Glycol 400 (PEG400) | 5, 1 | 3.0516 |
| SLS/Stearic Acid/PEG400 | 5, 1, 1 | 3.2821 |
| De-ionized Water | NA | 0.2733 |

Example 4

Formulation of Enhanced Dosage Forms

Figure 5:
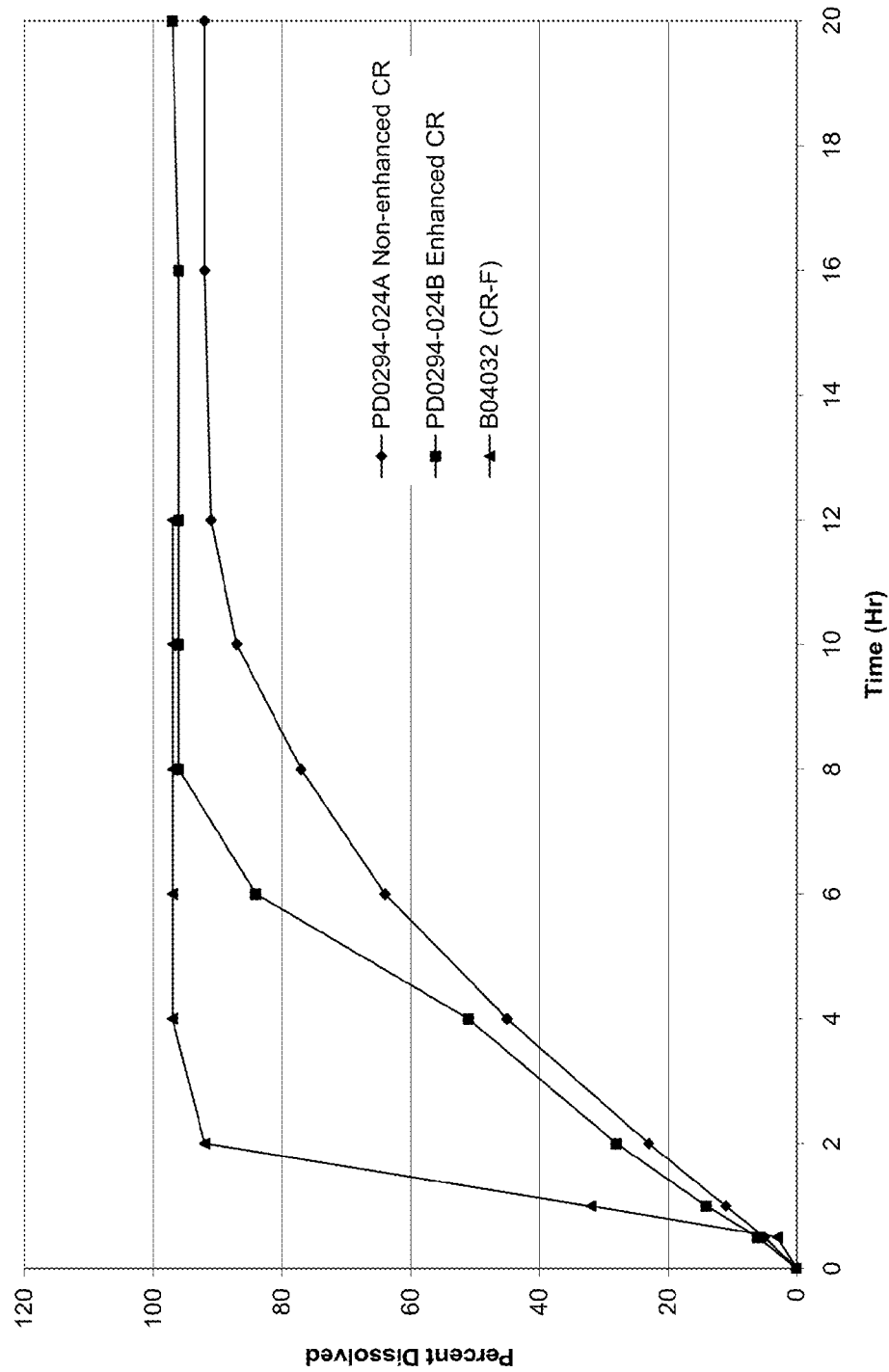
FIG. 5 shows the dissolution profiles of oxcarbazepine CR formulations with solubility enhancer (CRe), without solubility enhancer (CR) and a "fast formulation" (CR-F) developed in Example 1. The time to dissolve 80% of the drug ($T_{80}$) for CRe, CR, and CR-F are 5-6 Hrs, 8 Hrs, and 1.5 Hrs, respectively.
Figure 6:
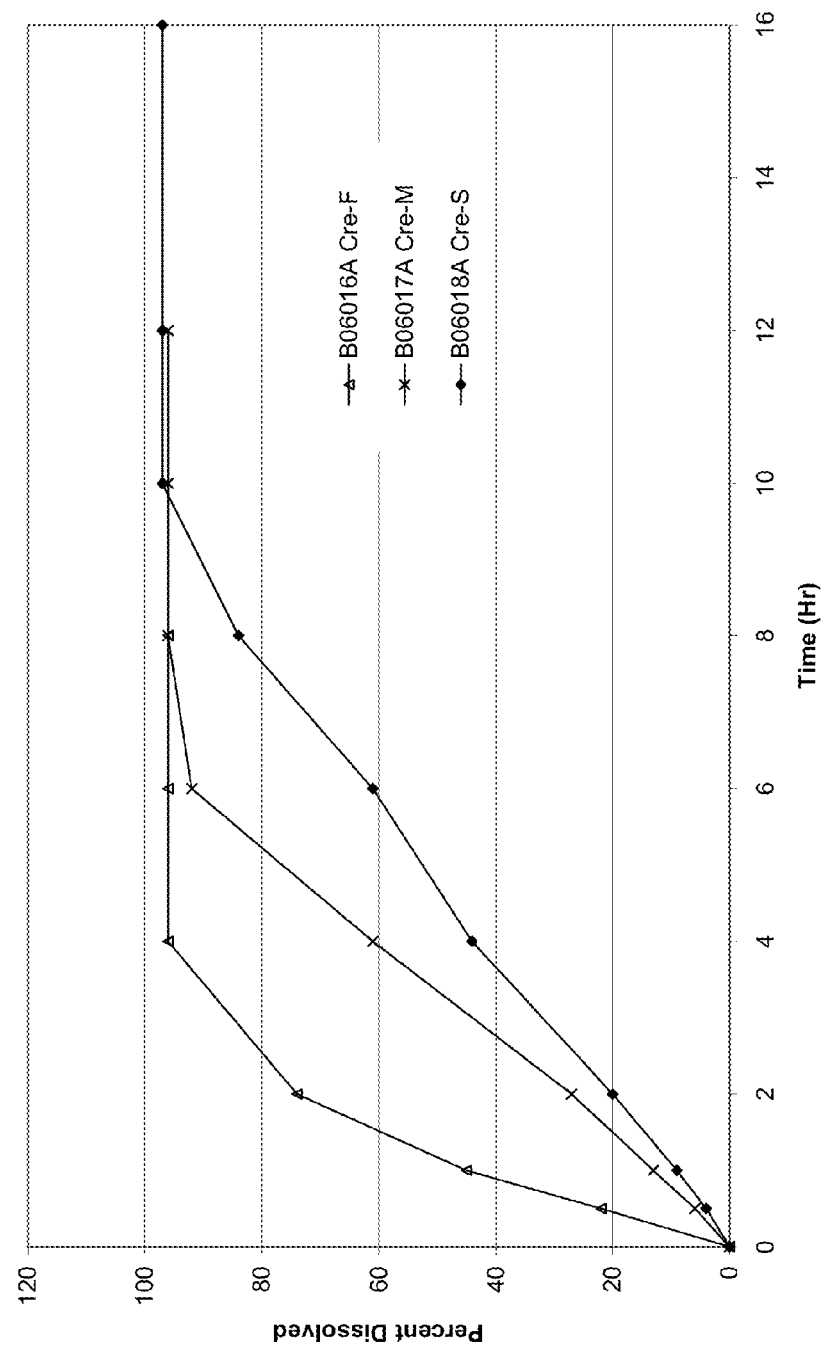
FIG. 6 shows the dissolution profiles for the fast (CRe-F), medium (CRe-M), and slow (CRe-S) oxcarbazepine formulations containing solubility/release enhancers. The $T_{80}$s for the CRe-F, CRe-M, and CRe-S are 1.5 Hrs, 5 Hrs, and 8 Hrs, respectively. USP Apparatus II at 60 RPM was used. Dissolution medium was 1% SLS in water.

Tables 4 and 5 provide the composition of the formulation containing solubility- and release-enhancing agents. Granules were manufactured by high shear granulation using water as the granulating liquid. All ingredients, except for magnesium stearate, were charged into a VG-65/10M high shear granulator. The dry powders were blended by running the blade for 3 minutes, upon which time water was sprayed onto the mixing blend at a spray rate of approximately 40-60 gm/min. After about a minute of spray, the chopper on the VG-65/10M was started and run throughout the spray. Once the granulation was completed, the granulation was discharged from the VG high shear granulator, spread on an appropriate tray and placed in an oven to dry at 40° C. for 24 Hrs. Alternatively, granules can be dried using a fluid bed processor. Dry granules are screened through an 18-mesh screen. Screened granules were blended with magnesium stearate in a proportion of 99.5% granules and 0.5% magnesium stearate. The resulting blend was then tableted on a rotary tablet press. Dissolution profiles for these formulations are shown in FIGS. 5 and 6.

TABLE 4

Percent Composition of Enhanced (CRe-M) and non-Enhanced (CR) Prototypes

| Formulation | % PD0294-005 Enhanced | % PD0294-008 Non-Enhanced |
|---|---|---|
| Oxcarbazepine | 60 | 60 |
| Prosolv SMCC50 | 10 | 25 |
| PVP K25 | 5 | 5 |
| HPMC K4M premium | 10 | 10 |
| SLS | 5 | 0 |
| Eudragit L100-55 | 10 | 0 |
| Magnesium Stearate | 0.5 | 0.5 |

TABLE 5

Percent Composition for the three exemplary enhanced formulations: CRe-F, CRe-M, and CRe-S.

| Formulation | % PD0294-046 CRe-F | % PD0294-051 CRe-M | % PD0294-054 CRe-S |
|---|---|---|---|
| Oxcarbazepine | 60 | 60 | 60 |
| Prosolv SMCC50 | 15 | 10 | 5 |
| PVP K25 | 5 | 5 | 5 |
| HPMC K4M premium | 5 | 10 | 15 |
| SLS | 5 | 5 | 5 |
| Eudragit L100-55 | 10 | 10 | 10 |
| Magnesium Stearate | 0.5 | 0.5 | 0.5 |

Example 5

Canine PK Studies on Formulations from Example 4, Table 4 and Example 1. (SLI530CR-F)

Figure 7:
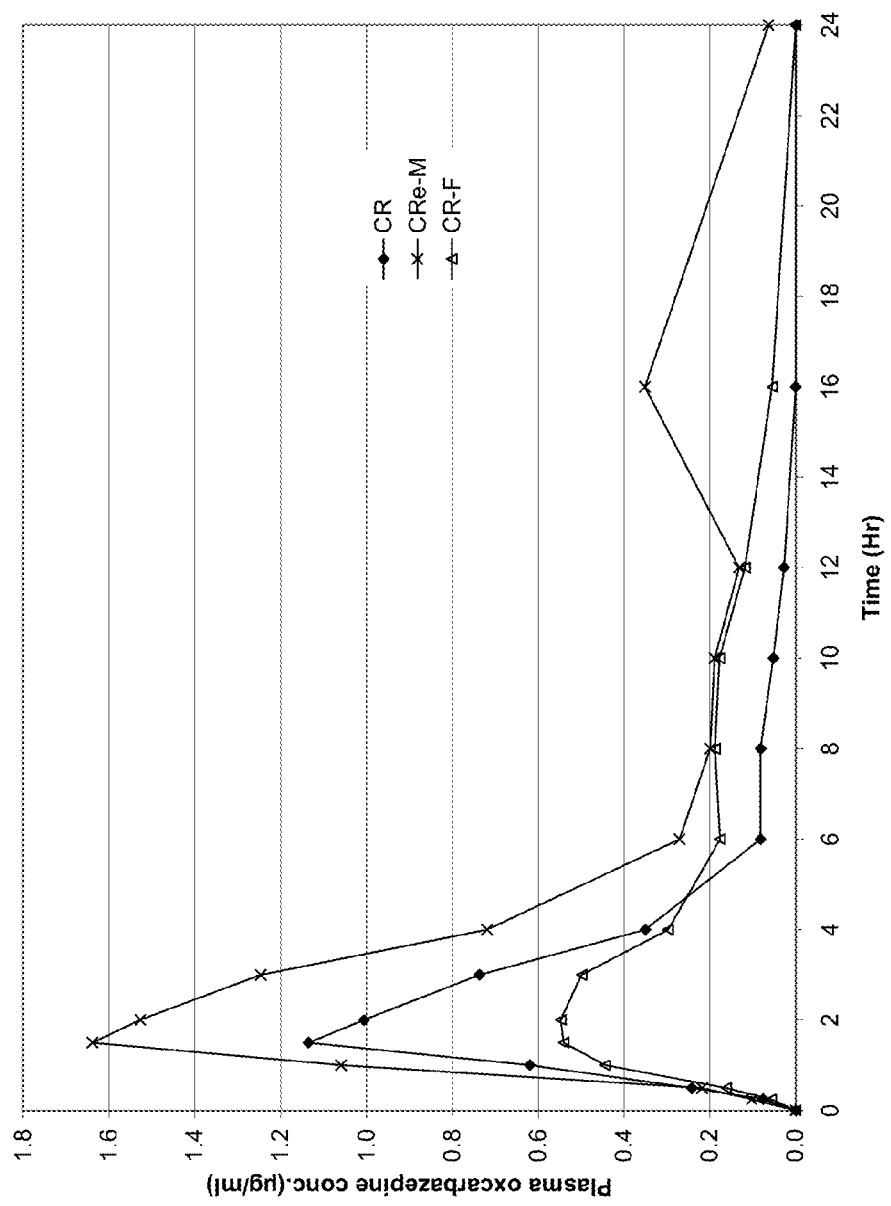
FIG. 7 shows the canine pharmacokinetic profiles with respect to oxcarbazepine, comparing the enhanced formulation (CRe) with non-enhanced formulations containing oxcarbazepine (CR and CR-F).
Figure 8:
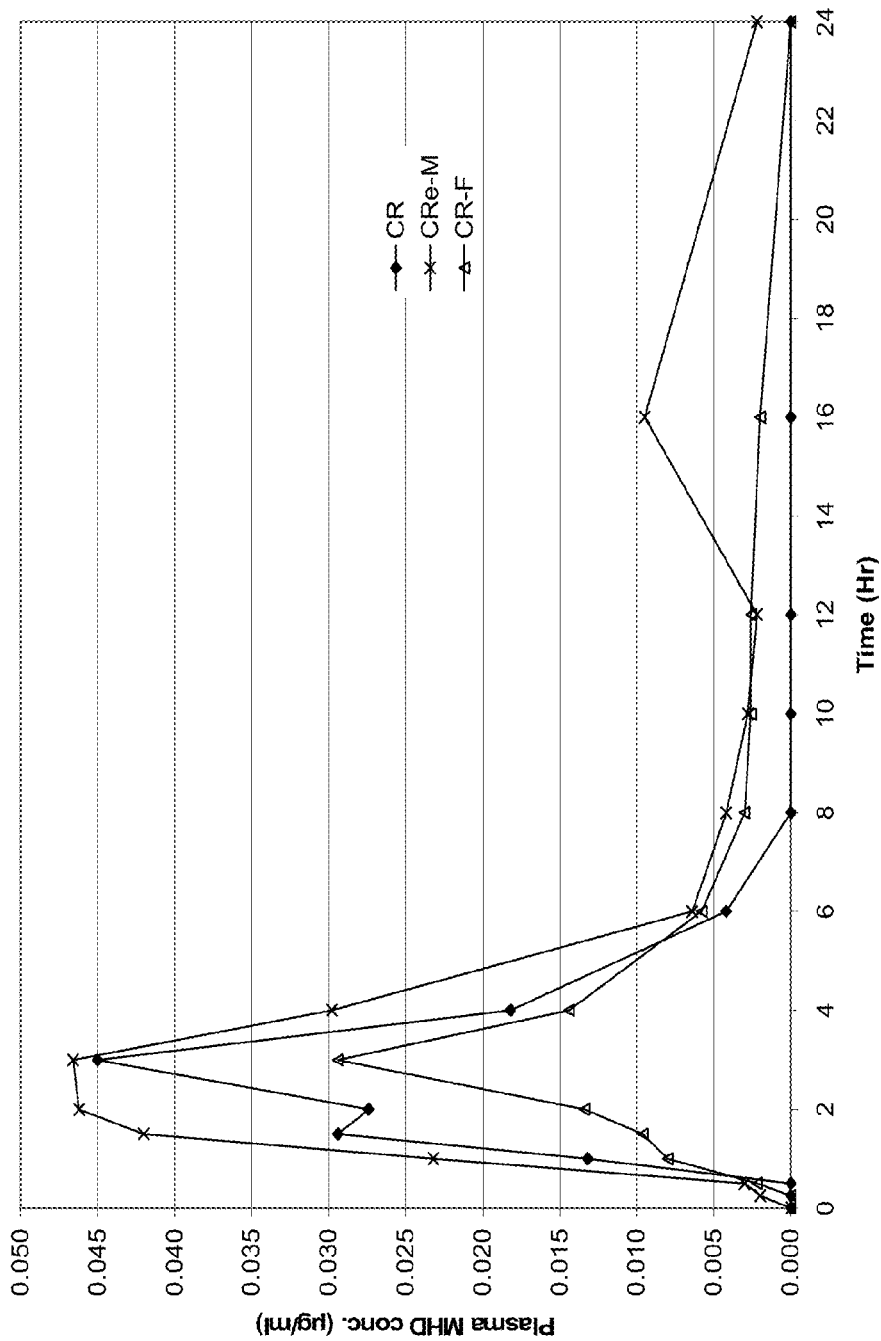
FIG. 8 shows the canine pharmacokinetic profiles with respect to MHD, comparing the enhanced formulation (CRe) with non-enhanced formulations containing oxcarbazepine (CR and CR-F).

Six male beagle dogs were dosed orally with the formulations in the order given in Table 6. Blood was drawn over a 24 Hr period and blood samples were analyzed by HPLC. A noncompartmental analysis of the data was used to generate $T_{max}$, $C_{max}$, $AUC_{last}$, and $AUC_{inf}$. Relative Bioavailability was calculated in Excel using the $AUC_{last}$ and $AUC_{inf}$ for the CRf formulation as the control. The PK profiles for oxcarbazepine and 10-hydroxycarbazepine are given in FIGS. 7 and 8.

TABLE 6

Prototypes tested in dogs

| Phase | Test Article | SLI Lot # | Dose (mg) |
|---|---|---|---|
| 1 | Oxcarbazepine CR | PD0294-024A | 600 |
| 2 | Oxcarbazepine CRe | PD0294-024B | 600 |
| 3 | Oxcarbazepine CR-F | B04032 | 600 |

TABLE 7

Canine pharmacokinetic profiles for enhanced, non-enhanced and control formulations of oxcarbazepine

| Prototypes | Non-Enhanced CR (CR) PD0294-024A | Enhanced CR (CRe-M) PD0294-024B | Fast CR (CR-F) B04032 |
|---|---|---|---|
| $T_{max}$ | 1.5 | 1.8 | 1.7 |
| $C_{max}$ | 1.20 | 1.72 | 0.7 |
| $AUC_{last}$ | 3.44 | 7.98 | 3.41 |
| $AUC_{inf}$ | 3.74 | 11.09 | 4.01 |
| Rel $BA_{last}$ | 101% | 234% | 100% |
| Rel $BA_{inf}$ | 93% | 276% | 100% |

Example 6

In Silico Modeling of Various Release Profiles of Oxcarbazepine XR

Figure 9:
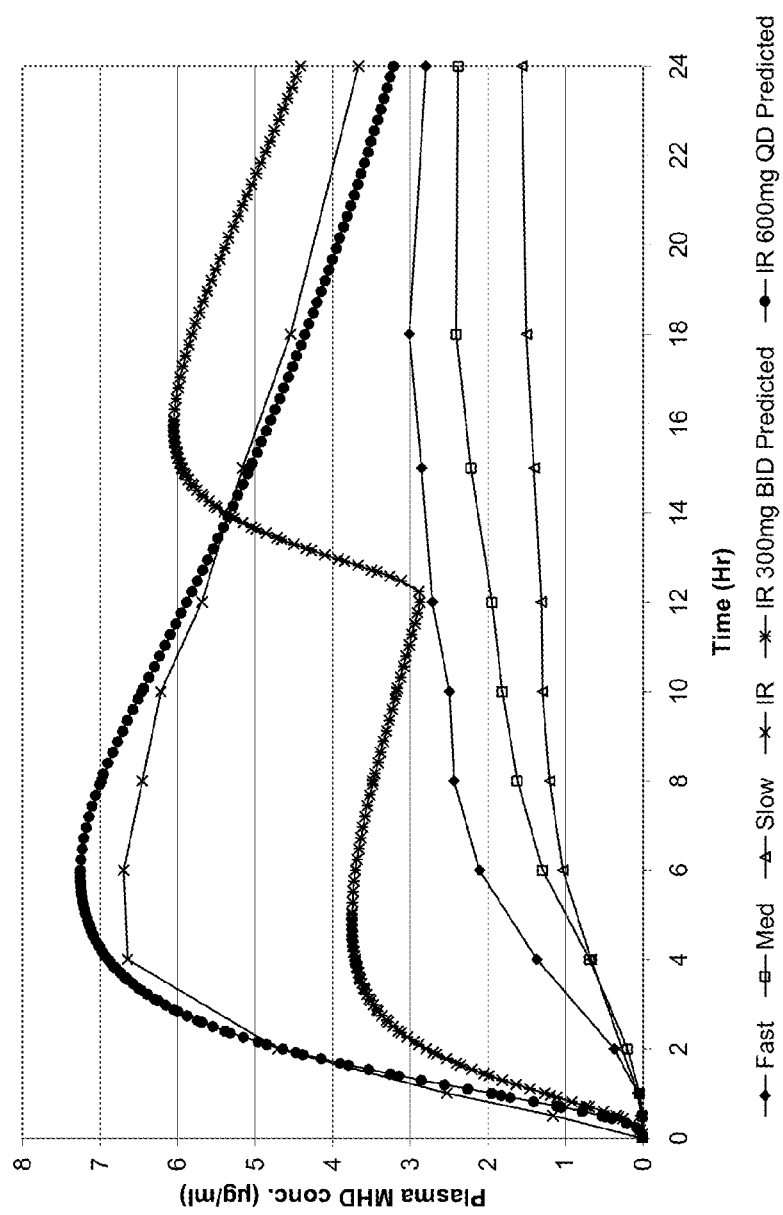
FIG. 9 shows the PK profiles shown in FIG. 8 with in silico predicted PK profile for a twice-a-day 300 mg IR.
Figure 10:
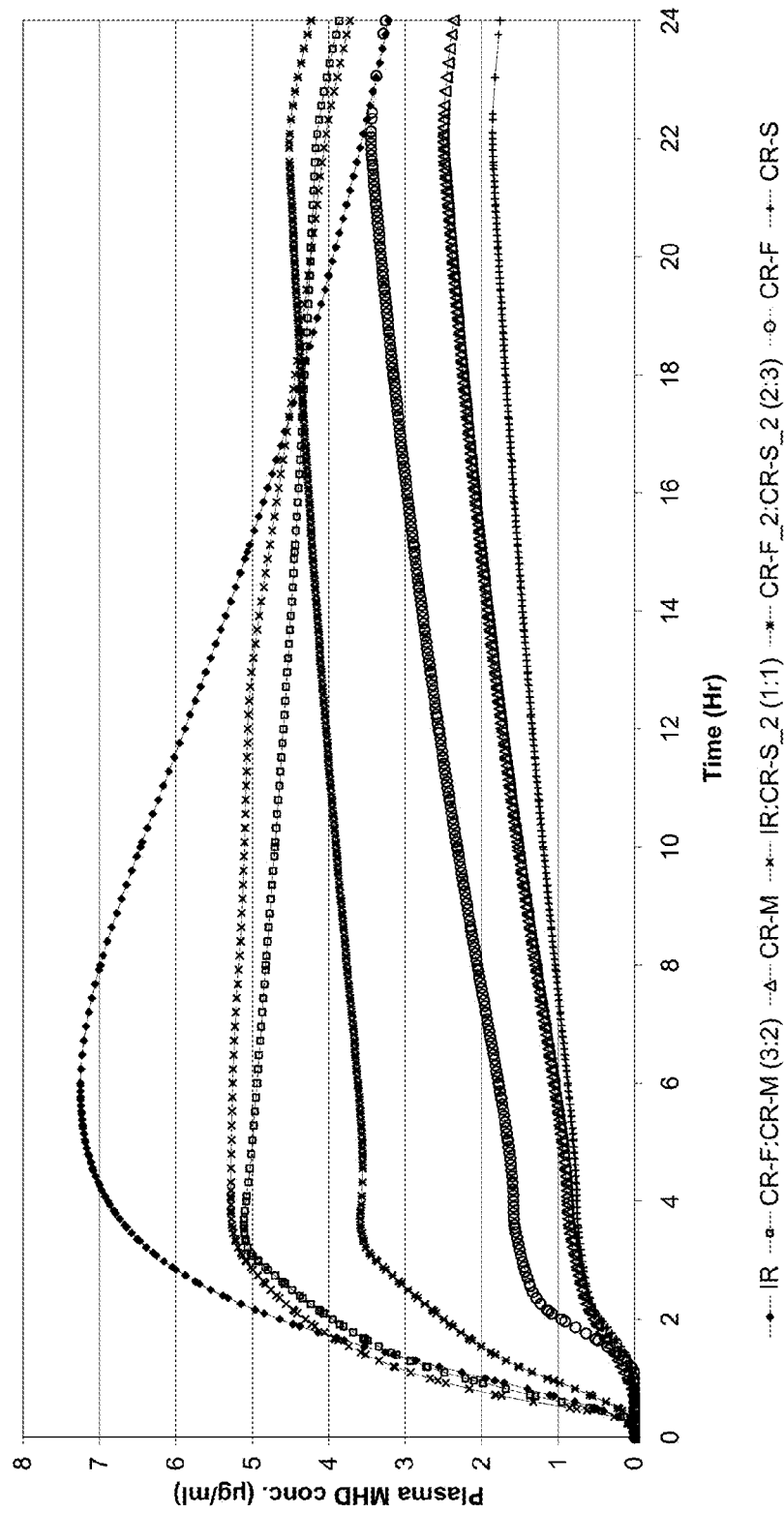
FIG. 10 shows in silico predicted PK profiles for various in vitro release profiles.
Figure 11:
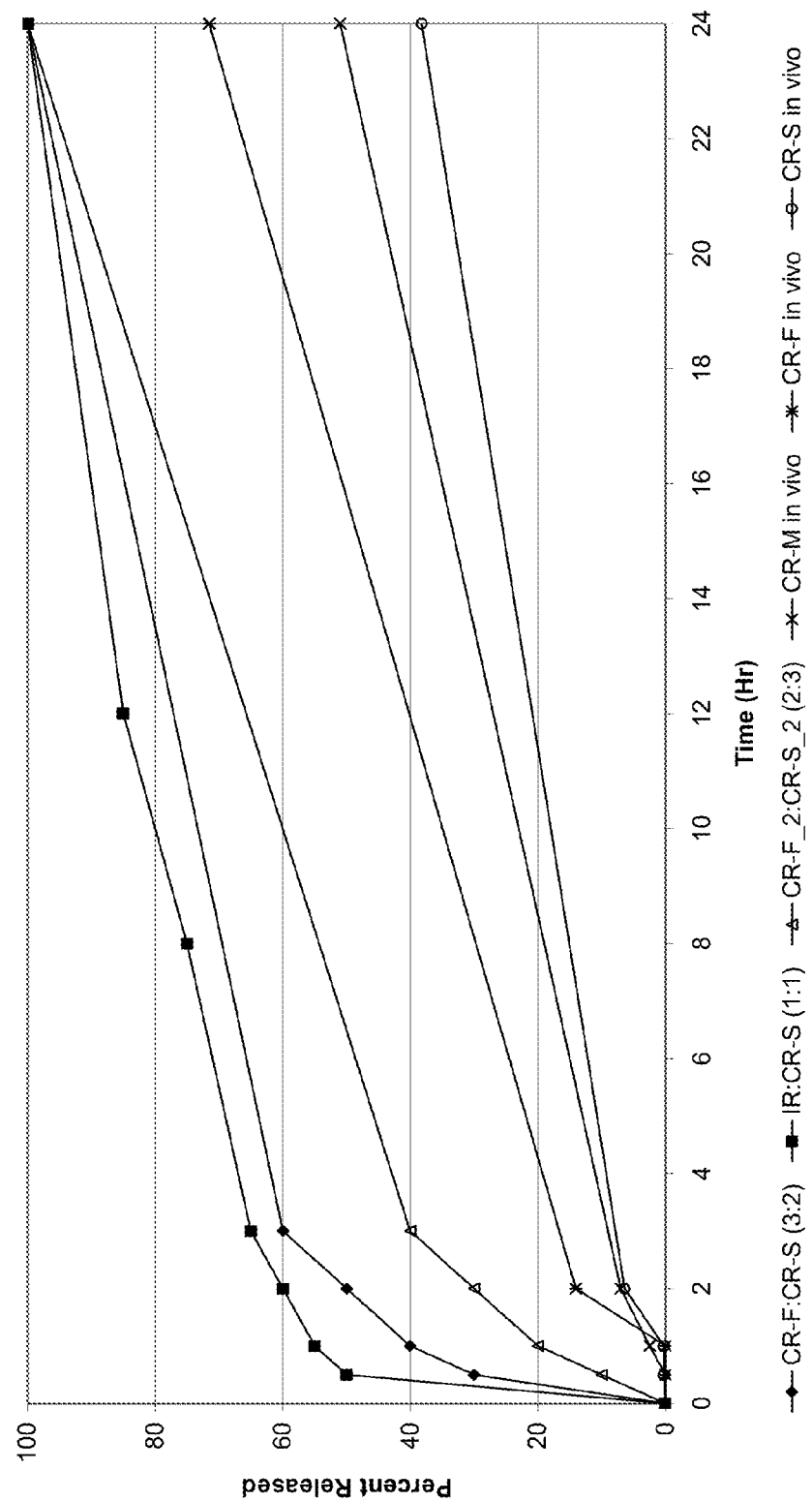
FIG. 11 shows the in silico predicted in vivo release profiles for the systems in FIG. 10.

In silico modeling was carried out for various hypothetical systems. Results are shown in FIGS. 9-11.

Example 7

Human Pharmacokinetic Evaluation of Solubility Enhanced Oxcarbazepine CR Formulations from Example 4

The three solubility enhanced prototypes from the Example 4 were evaluated in humans to obtain pharmacokinetic information. An immediate release tablet (Trileptal® 300 mg) given BID was used as a reference. The formulations were examined in a randomized, single dose, crossover study in healthy human volunteers. Blood samples were analyzed for both the parent molecule oxcarbazepine and its metabolite (the monohydroxy derivative, MHD).

Figure 12:
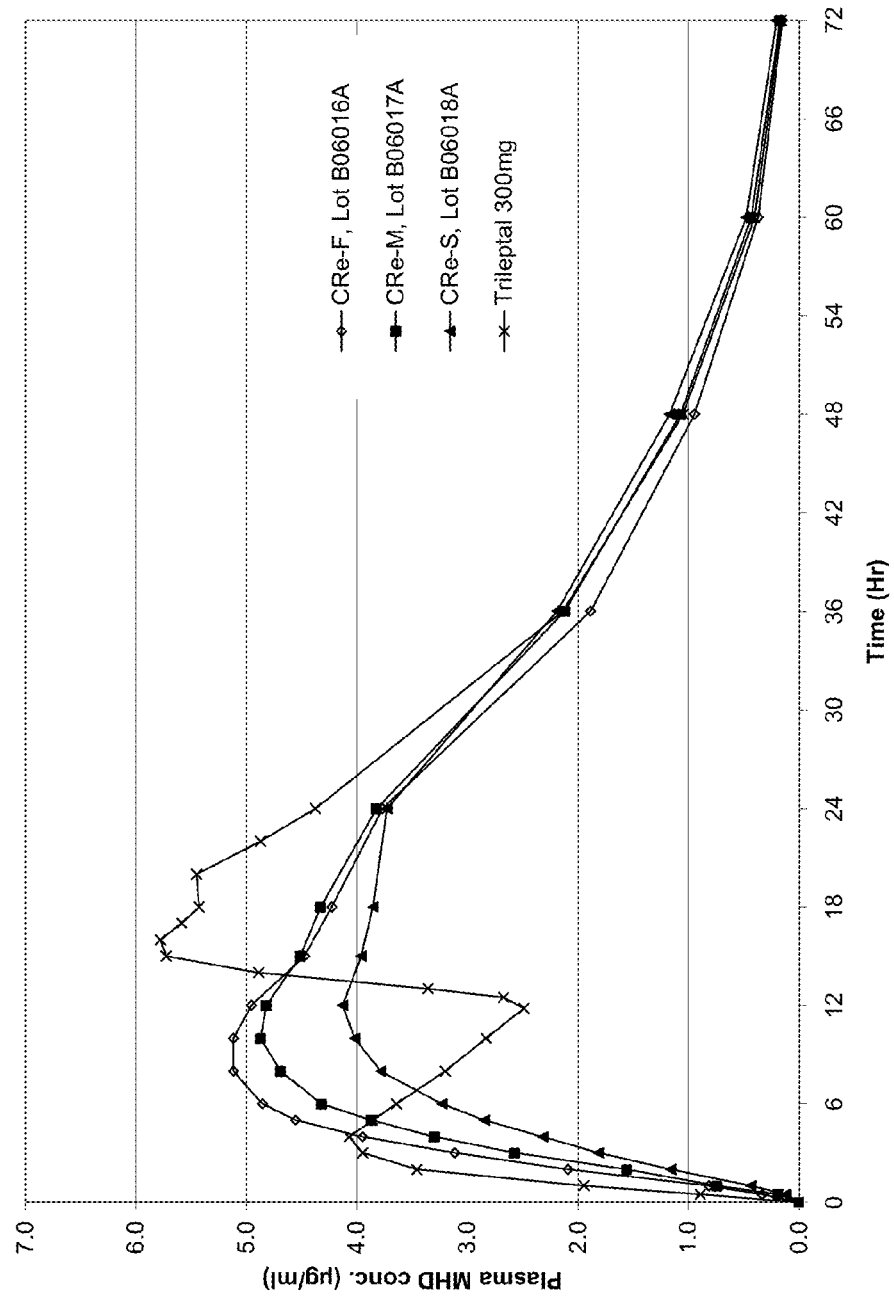
FIG. 12 shows human plasma concentration vs. time profiles with respect to MHD of the three Oxcarbazepine CR formulations in Example 4 (CRe-F, CRe-M, CRe-S) and Trileptal® as an IR control, dosed BID.
Figure 13:
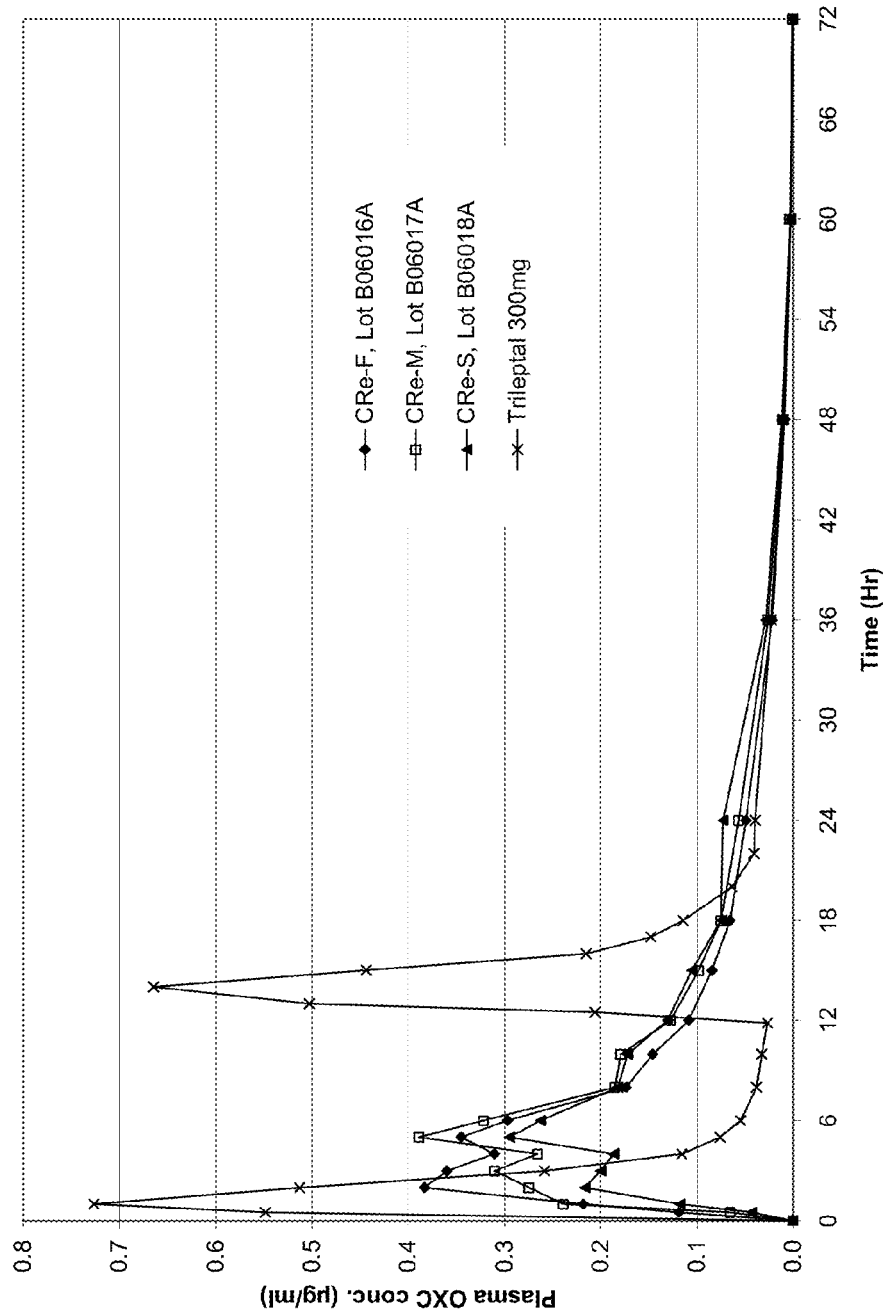
FIG. 13 shows human plasma concentration vs. time profiles with respect to the oxcarbazepine of the three Oxcarbazepine CR formulations in Example 4 (CRe-F, CRe-M, CRe-S) and Trileptal® as an IR control, dosed BID.
Figure 14:
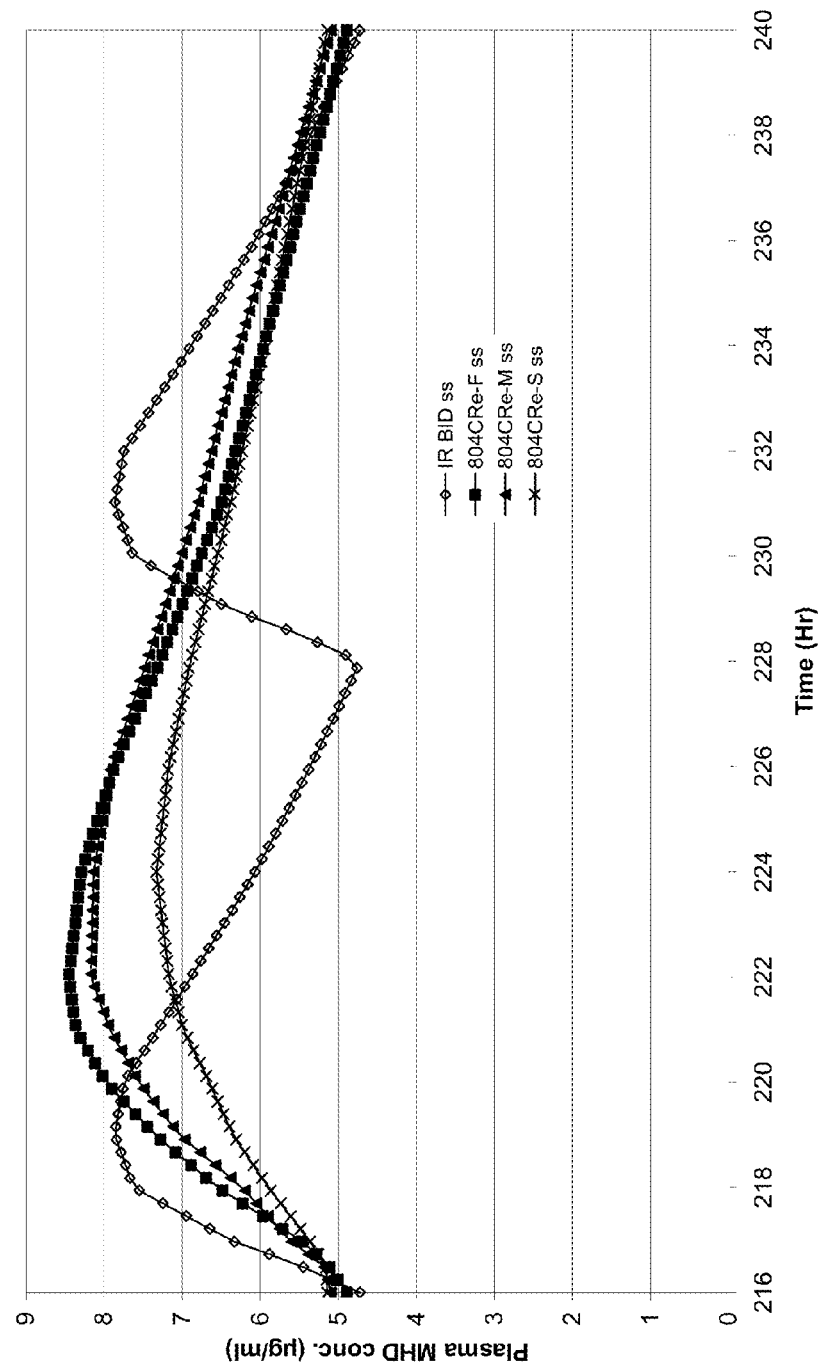
FIG. 14 shows the in silico predicted steady-state plasma profiles for the three exemplary formulations (CRe-F, CRe-M, and CRe-S) described in Example 4.

Table 8 provides the mean PK parameters for MHD. The PK profiles are shown in FIGS. 12 and 13.

TABLE 8

Pharmacokinetic parameters of the three exemplary solubility enhanced formulations in Example 4 and Trileptal ™

| PK Parameters | CRe-F Fast | CRe-M Med | CRe-S Slow | Trileptal ™ BID |
|---|---|---|---|---|
| $T_{max}$ (Hr) | 9 | 11 | 14 | 16 |
| $C_{max}$ (ug/mL) | 5.32 | 5.14 | 4.40 | 6.23 |
| $AUC_{last}$ (Hr*ug/mL) | 160.3 | 161.3 | 148.9 | 167.1 |
| Rel BA | 96% | 97% | 89% | 100% |

What is claimed is:

1. A pharmaceutical formulation for once-a-day administration of oxcarbazepine comprising multiple units, wherein each unit comprises a homogeneous mixture of:
 (a) oxcarbazepine;
 (b) 1-50%, by weight of the formulation, a matrix-forming polymer;
 (c) 1-80%, by weight of the formulation, at least one agent that enhances the solubility of oxcarbazepine; and
 (d) 10-90%, by weight of the formulation, at least one release promoting agent comprising a polymer having pH-dependent solubility selected from the group consisting of cellulose acetate phthalate, cellulose acetate succinate, methylcellulose phthalate, ethylhydroxycellulose phthalate, polyvinylacetate phthalate, polyvinyl butyrate acetate, vinyl acetate-maleic anhydride copolymer, styrene-maleic mono-ester copolymer, Eudragit L100-55 (Methacrylic Acid-Ethyl Acrylate Copolymer (1:1)), and methyl acrylate-methacrylic acid copolymers.

2. The formulation of claim 1, wherein the matrix-forming polymer is selected from the group consisting of cellulosic polymers, alginates, gums, cross-linked polyacrylic acid, carageenan, polyvinyl pyrrolidone, polyethylene oxides, and polyvinyl alcohol.

3. The formulation of claim 2, wherein the cellulosic polymers are selected from the group consisting of hydroxypropylmethylcellulose (HPMC), hydroxypropylcellulose (HPC), hydroxyethylcellulose (HEC), methylcellulose (MC), powdered cellulose, cellulose acetate, sodium carboxymethylcellulose, calcium salt of carboxymethylcellulose, and ethylcellulose.

4. The formulation of claim 1, wherein the agent that enhances the solubility of oxcarbazepine selected from the group consisting of surface active agents, complexing agents, cyclodextrins, pH modifying agents, and hydration promoting agents.

5. The formulation of claim 4, wherein the surface active agents comprise sodium docusate, sodium lauryl sulfate, sodium stearyl fumarate, polyethylene oxide (PEO) modified sorbitan monoesters, fatty acid sorbitan esters, polyethylene oxide-polypropylene oxide-(poly(ethylene oxide)) block copolymers, or combinations thereof.

6. The formulation of claim 1, wherein the polymer having pH dependent solubility remains intact at pH values of below 4 and dissolves at pH values of more than 4.

7. The formulation of claim 6, wherein the polymer having pH dependent solubility dissolves at pH values of more than 5.

8. The formulation of claim 7, wherein the polymer having pH dependent solubility dissolves at pH values of more than 6.

9. The formulation of claim 1, wherein the rate of release of oxcarbazepine from the formulation in vitro over time is sigmoidal.

10. The formulation of claim 1, wherein the matrix-forming polymer is incorporated in an amount from 1% to 50% by weight of the formulation, and the agent that enhances the solubility of oxcarbazepine is incorporated in an amount from 1% to 80% by weight of the formulation.

11. The formulation of claim 1, further comprising a lubricant selected from the group consisting of magnesium stearate, calcium stearate, zinc stearate, stearic acid, polyethylene glycol, leucine, glyceryl behenate, sodium stearyl fumarate, hydrogenated vegetable oils, and waxes.

12. The formulation of claim 11, wherein the wax is selected from the group consisting of beeswax, carnuba wax, cetyl alcohol, glyceryl stearate, glyceryl palmitate, and stearyl alcohol.

13. The formulation of claim 11, wherein the lubricant is incorporated in an amount of from 0.1% to 20% by weight of the formulation.

14. The formulation of claim 1, wherein the amount of oxcarbazepine is effective to produce a steady state blood level of monohydroxy derivative of oxcarbazepine in the range of about 2 µg/ml to about 10 µg/ml.

15. The formulation of claim 1, wherein the formulation is effective in minimizing fluctuations between $C_{min}$ and $C_{max}$ of monohydroxy derivative of oxcarbazepine.

16. The formulation of claim 15, which provides $C_{max}$ levels of monohydroxy derivative of oxcarbazepine in the range of about 6 µg/ml to about 10 µg/ml and $C_{min}$ levels of monohydroxy derivative of oxcarbazepine in the range of about 2 µg/ml to about 5 µg/ml.

17. The formulation of claim 1, wherein the amount of oxcarbazepine is 600 mg.

18. The formulation of claim 1, in the form of pellets, tablets, granules or capsules.

19. The formulation of claim 18, in the form of tablets.

20. The formulation of claim 19, wherein each tablet comprises 600 mg of oxcarbazepine.

* * * * *